(12) United States Patent
Hoeg et al.

(10) Patent No.: US 6,371,909 B1
(45) Date of Patent: Apr. 16, 2002

(54) APPARATUS AND METHOD FOR PROVIDING SPHERICAL VIEWING DURING ENDOSCOPIC PROCEDURES

(75) Inventors: Hans D. Hoeg, La Crescenta; Joel W. Burdick, Pasadena; Andrew B. Slatkin, Tarzana, all of CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/252,654

(22) Filed: Feb. 19, 1999

Related U.S. Application Data

(60) Provisional application No. 60/076,377, filed on Feb. 19, 1998, and provisional application No. 60/081,780, filed on Apr. 14, 1998.

(51) Int. Cl.[7] .................................................. A61B 1/04
(52) U.S. Cl. ..................... 600/173; 600/112; 600/117
(58) Field of Search ........................ 600/109, 111, 116, 129, 112, 160, 117, 173, 174; 348/65, 82–85

(56) References Cited

U.S. PATENT DOCUMENTS

| | | |
|---|---|---|
| 1,726,268 A | 8/1929 | Jahr |
| 2,002,595 A | 5/1935 | Wappler |
| 2,793,639 A | 5/1957 | Roberge |
| 2,987,960 A | 6/1961 | Sheldon |
| 3,075,516 A | 1/1963 | Strauch |
| 3,096,756 A | 7/1963 | Rosenfeld et al. |
| 3,270,641 A * | 9/1966 | Gosselin ..................... 385/118 |
| 3,614,891 A | 10/1971 | Nolte |
| 3,773,039 A | 11/1973 | Mori et al. |
| 3,804,081 A | 4/1974 | Kinoshita et al. |
| 3,835,841 A * | 9/1974 | Terada ......................... 600/157 |
| 3,856,000 A | 12/1974 | Chikama |
| 3,880,148 A | 4/1975 | Kanehira et al. |
| 3,889,662 A | 6/1975 | Mitsui |
| 3,918,438 A | 11/1975 | Hayamizu et al. |
| 4,078,555 A | 3/1978 | Takahashi |
| 4,140,364 A | 2/1979 | Yamashita et al. |
| 4,277,168 A | 7/1981 | Oku |
| 4,286,585 A | 9/1981 | Ogawa |
| 4,292,961 A | 10/1981 | Kawashima |
| 4,557,598 A | 12/1985 | Ono et al. |
| 4,697,577 A * | 10/1987 | Forkner ....................... 600/173 |
| 4,783,156 A | 11/1988 | Yokota |
| 4,838,247 A | 6/1989 | Forkner |
| 4,846,154 A | 7/1989 | MacAnally et al. |
| 5,363,839 A * | 11/1994 | Lankford ..................... 600/112 |
| 5,495,370 A * | 2/1996 | Tuffen ......................... 359/402 |
| 5,573,493 A | 11/1996 | Sauer et al. |
| 5,584,793 A | 12/1996 | Sauer et al. |
| 5,643,176 A | 7/1997 | Persidsky |
| 5,899,851 A * | 5/1999 | Koninckx ................... 600/129 |
| 5,976,074 A * | 11/1999 | Moriyama ................... 600/144 |
| 6,097,423 A * | 8/2000 | Mattsson-Boze et al. ..... 348/65 |

FOREIGN PATENT DOCUMENTS

| | | |
|---|---|---|
| DE | 297 18 058 U1 | 1/1998 |
| EP | 0 096 761 A1 | 12/1983 |
| EP | 0 251 478 A1 | 1/1988 |
| WO | WO 90/04350 | 5/1990 |

* cited by examiner

Primary Examiner—John P. Leubecker
(74) Attorney, Agent, or Firm—Fulwider Patton Lee & Utecht, LLP

(57) ABSTRACT

The present invention is an improved apparatus and method for providing variable-angle endoscopic views in a cavity, such as an internal cavity in a human patient. The apparatus includes an elongated tubular portion with a viewer at its proximal end and a reflector assembly at its distal end. The reflector assembly includes a first reflector and a second reflector, with the second reflector rotationally mounted to permit its rotation about an axis generally aligned with an optical path portion passing from the first reflector to the second reflector. The viewer is preferably a camera rotatably secured to the apparatus. A rotator controls rotation of the second reflector and the camera, so that rotation of the second reflector causes a corresponding rotation of the camera. The assembly thus permits near-spherical viewing of the cavity without requiring substantial movement of the endoscope.

14 Claims, 13 Drawing Sheets

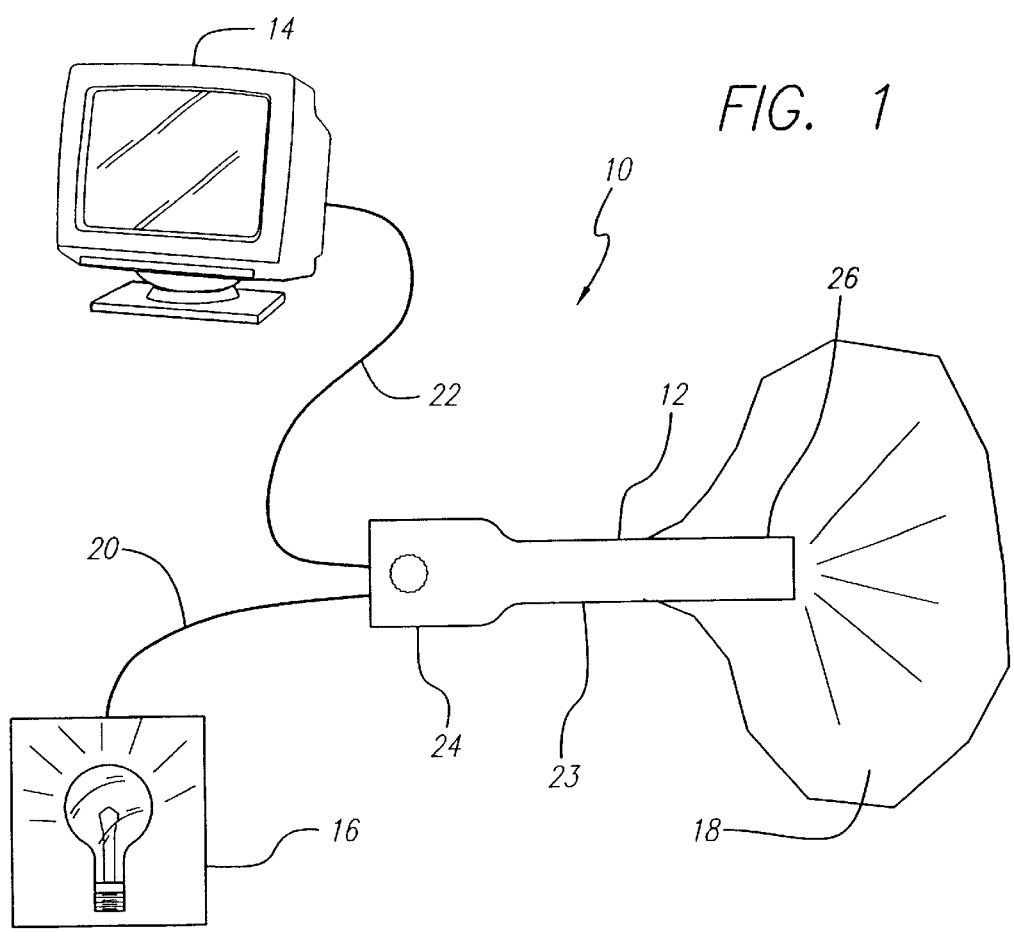
FIG. 1
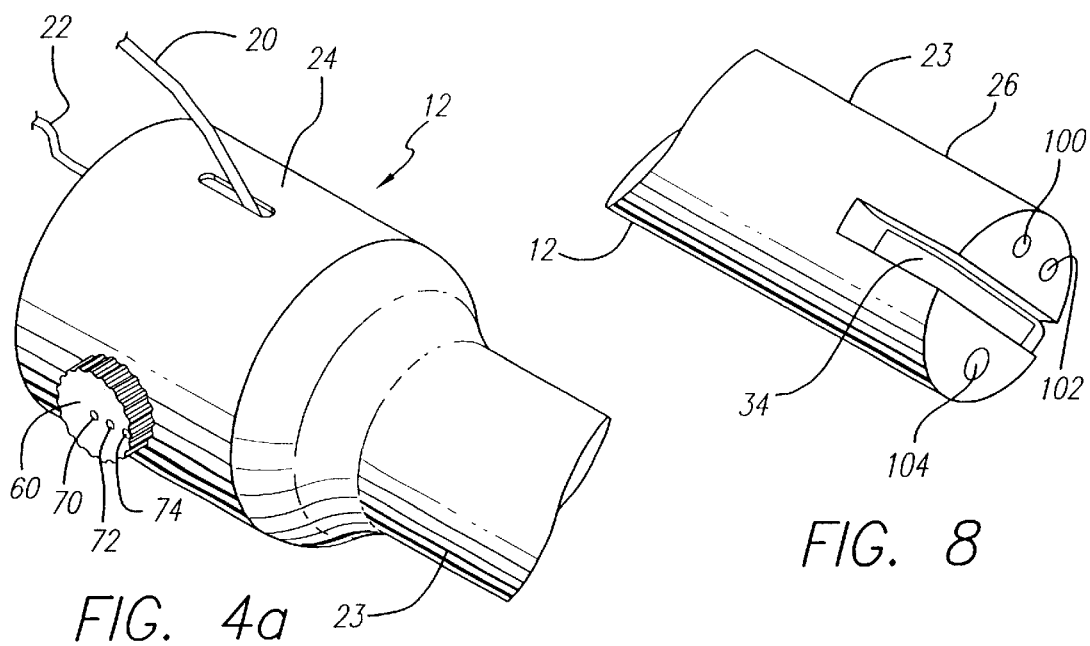
FIG. 4a
FIG. 8

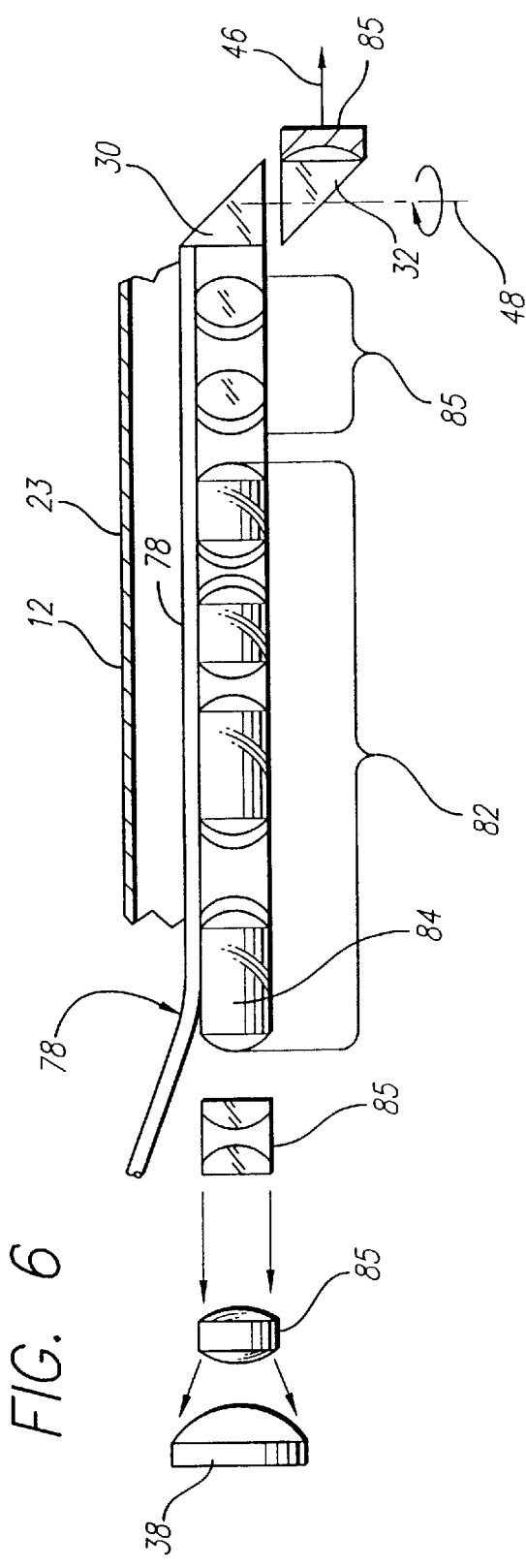
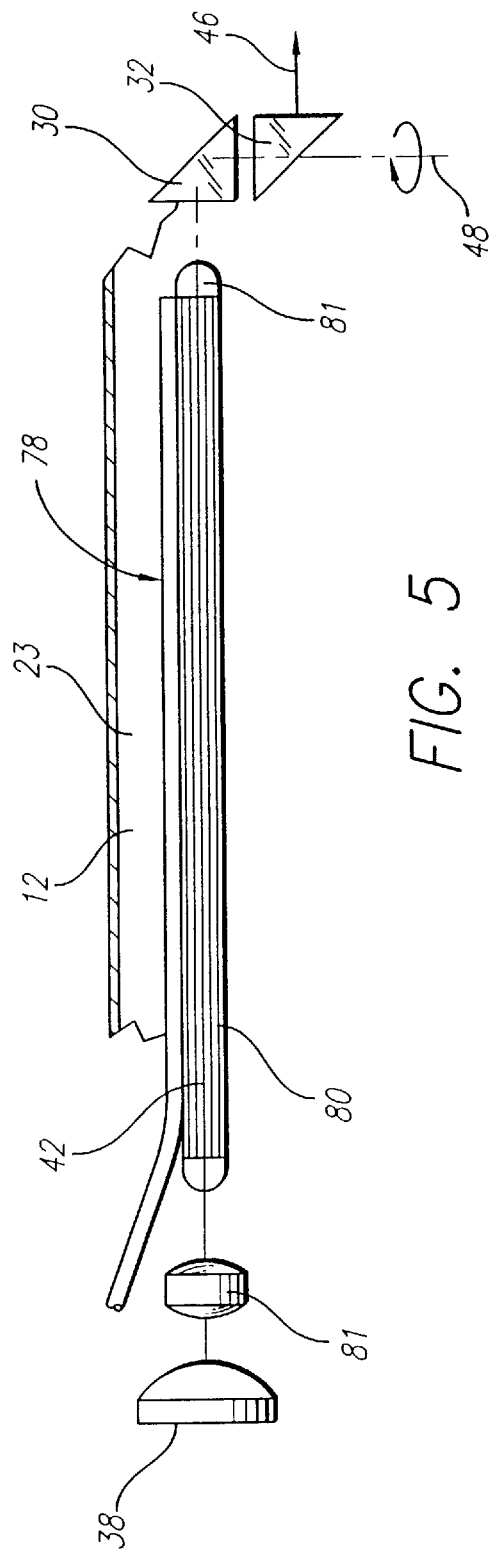
FIG. 6
FIG. 5

APPARATUS AND METHOD FOR PROVIDING SPHERICAL VIEWING DURING ENDOSCOPIC PROCEDURES

REFERENCE TO RELATED APPLICATIONS

This application is related to and claims the benefit of U.S. Provisional Application No. 60/076,377, filed Feb. 19, 1998, and U.S. Provisional Application No. 60/081,780, filed Apr. 14, 1998.

BACKGROUND OF THE INVENTION

1. Field of the Invention

This invention relates generally to viewing systems and, more particularly, to an apparatus and method for providing spherical viewing in a cavity, such as an internal body cavity of a patient.

2. Description of the Related Art

Minimally invasive surgery (MIS) such as laparoscopic, endoscopic, hysteroscopic, and arthroscopic surgery (referred to hereafter generally as endoscopic surgery), is becoming more widely used because it is often less traumatic to the patient, generally involves less hospitalization time, less discomfort, and less risk to the patient, and is usually less costly than traditional open surgery.

The endoscopic surgery is generally preformed using elongate instruments slidably inserted through an opening into a body cavity. If the body cavity is accessible through a naturally occurring body orifice, the instruments may be inserted through that orifice. In cases where the body cavity is otherwise inaccessible, a small incision may be created in the patient to provide access to the area to be treated. A trocar sheath may be inserted in the incision, with the trocar heath configured to permit the slidable insertion and rotation of endoscopes and surgical instruments into the cavity.

An endoscope is generally used to view the inside of the body cavity. For example, an endoscope can be used to inspect the condition of the tissue lining a body organ, such as a human uterus. The endoscope can also be used to observe the manipulations being performed by surgical instruments positioned within the body cavity. Most current endoscopes provide a limited and fixed view, so that the surgeon typically must physically reposition the entire endoscope in order to change the endoscopic view within the body cavity, or remove the endoscope entirely and replace it with one having the desired angle of view. Such manipulations and replacements can be undesirable, since they can complicate the surgery and increase the risk of inadvertent damage to body tissue from accidental contact between the tissue and the endoscope.

Several previous designs have been proposed to permit individual endoscopes to vary their angles of view without requiring extensive movement of the endoscope. The small sizes of endoscopes, which can be on the order of 3 mm in diameter, place restrictions on such designs, and limit the options available. For example, complicated combinations of optics may be difficult to assemble in the small enclosure provided by the body of many endoscopes.

Therefore, those concerned with the development and use of endoscopic surgical systems and the like have long recognized the need for a system which is capable of enabling a surgeon to efficiently view large portions of internal cavities without requiring large manipulations or replacements of endoscopes during a procedure. Accordingly, the present invention fulfills these needs by providing an efficient and effective endoscope apparatus, selectively operable to permit a surgeon to view the majority of the internal area without having to replace or make major movements of the endoscope.

SUMMARY OF THE INVENTION

Briefly, and in general terms, the present invention provides a new and improved viewing system, apparatus, and method for viewing internal cavities, such as an internal opening in a human body.

The present invention provides an endoscope or similar viewing apparatus that permits near-spherical viewing of a cavity, such as an internal enclosure, a crevass, or other generally inaccessible area. The invention permits such viewing without requiring large movements of the endoscope. The apparatus includes a distal portion with distal viewing optics, such as reflectors or cameras, that collect images from the cavity interior. The images are then relayed to the proximal portion of the apparatus, where they can be viewed by a user or relayed to an external display.

By moving an internal reflector within the distal portion of the endoscope, the endoscope can vary its angle of view from 0 degrees (i.e., straight ahead from the endoscope distal end) to as much as plus or minus 180 degrees (i.e., looking back toward the proximal portion of the endoscope), depending on the particular design. Rotation of the endoscope distal viewing optics about the endoscope's longitudinal axis, such as may be accomplished by rotating the entire endoscope about its longitudinal axis, when combined with the previously discussed angle-varying optical procedure, permits the endoscope to achieve near-spherical viewing of the interior of the body cavity, without requiring the endoscope to undertake any movement except a simple rotation about its longitudinal axis. Moreover, where the endoscope is surrounded by or otherwise includes an outer sheath that remains stationary during such rotations, the movement of the interior portions of the endoscope (to permit spherical viewing) can be conducted with the outer sheath remaining stationary, thus preventing any potential damage to tissue that may be in contact with the outer sheath.

The invention further provides improved feedback to the user regarding the line of sight along which the system is viewing. The feedback may be provided on a monitor or via directional control mechanisms, such as a rotator knob positioned on the endoscope.

These and other features of the invention will become apparent from the following detailed description, when taken in conjunction with the accompanying drawings.

BRIEF DESCRIPTION OF THE DRAWINGS

FIG. 1 is a view of an endoscopic viewing system according to an embodiment of the invention;

FIG. 4a is a perspective view of a proximal portion of an endoscope in accordance with an embodiment of the invention;

FIG. 5 is a cross-sectional side view of an endoscope, according to an embodiment of the invention;

FIG. 6 is a cross-sectional side view of an endoscope, according to an embodiment of the invention;

FIG. 8 is a cross-sectional side view of a distal portion of an endoscope, according to an embodiment of the invention;

FIGS. 9b and 9c are cross-sectional views of the endoscope depicted in FIG. 9a;

DETAILED DESCRIPTION OF THE PREFERRED EMBODIMENTS

Figure 2:
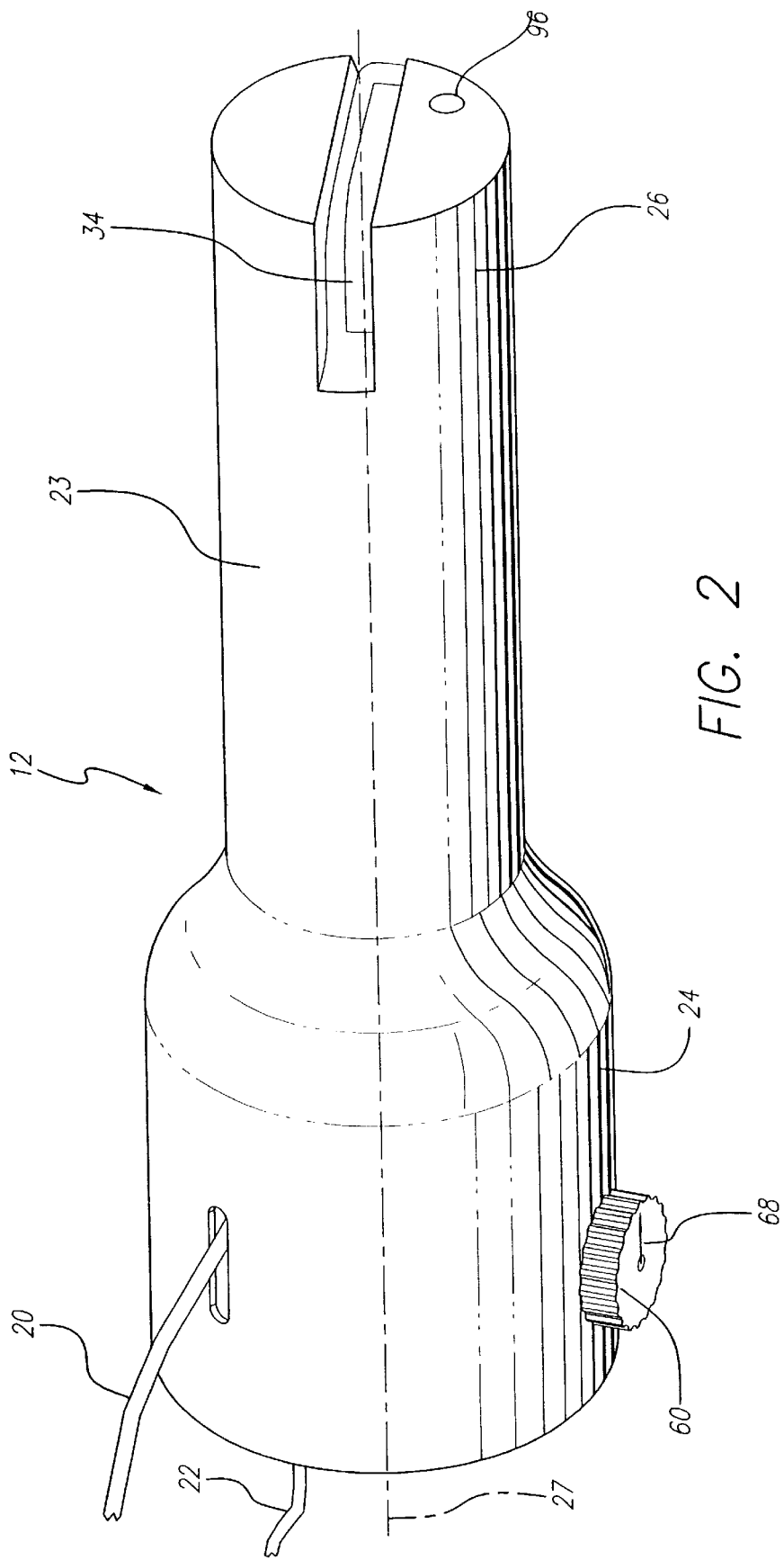
FIG. 2 is a perspective view of an endoscope according to an embodiment of the invention.

Referring now to the drawings with more particularity, wherein like reference numerals in the separate views indicate like or corresponding elements, there is shown in FIG. 1 a system 10 for endoscopic viewing. The endoscopic system 10 includes an endoscope 12, a monitor 14 for viewing images received from the endoscope 12, and an illumination source 16 for providing illumination to the area being viewed by the endoscope 12.

In typical usage, the endoscope 12 is inserted into a cavity 18 or other area to be viewed, such as a human body cavity. The endoscope receives illumination from the illumination source 16, with the illumination passing through a light-transmitting cable 20, such as a fiber-optic cable or the like, to the endoscope 12 and into the cavity 18 to illuminate desired portions of the cavity.

Although the embodiment depicted in FIG. 1 has the illumination source 16 outside of the endoscope 12, the illumination source may be positioned on or within the endoscope itself. For example, a small light source, such as an LED or small light bulb, may be positioned on or within the endoscope in a position that permits the light to travel, either directly or through reflectors or fiber-optic cables and the like, to shine on desired portions of the cavity.

In FIG. 1, the monitor 14 receives image signals from the endoscope 12. In the embodiment depicted, the images are transmitted to the monitor 14 via one or more cables 22 passing from the endoscope 12 to the monitor 14.

Figure 3:
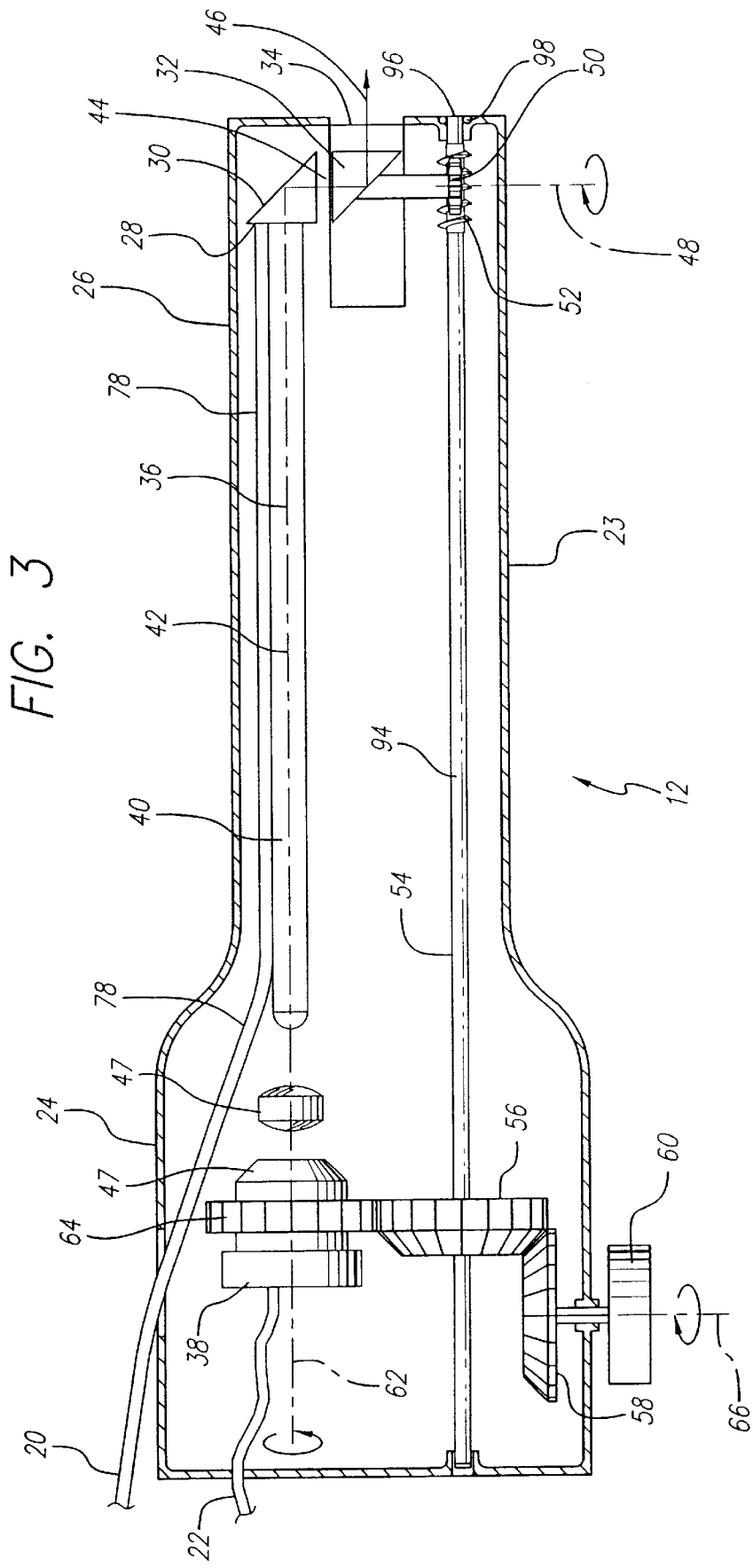
FIG. 3 is a cross-sectional side view of the endoscope depicted in FIG. 2, according to an embodiment of the invention.

FIGS. 2 and 3 show in greater detail an embodiment of an endoscope in accordance with the invention. As depicted in FIGS. 2 and 3, the endoscope 12 has a generally tubular shaft 23, with an enlarged proximal end portion 24 and a distal end portion 26. In use, the user can grasp the endoscope 12 by its proximal end portion 24 and insert the distal end portion 26 into the cavity 18. The endoscope 12 can be rotated about its longitudinal axis 27 to provide some control of the viewing direction.

The distal end portion 26 includes an optical assembly 28 positioned inside. The optical assembly 28 comprises a first reflector 30 and a second reflector 32, which in the embodiment depicted are both prisms. The distal end portion 26 includes a window 34 through which the second reflector receives light (and images) from the outside of the endoscope 12. In the embodiment of FIGS. 2 and 3, the window 34 comprises a clear layer of material that seals the endoscope against fluids and other debris while admitting light for viewing the interior of the body cavity. Such a lens may be formed of various materials, such as plastic, glass, or other materials, depending on the desired application. In other embodiments, the window may simply comprise an unobstructed opening in the distal end portion 26 of the endoscope 12.

The first reflector 30 and second reflector 32 are positioned in the endoscope so as to define an optical path 36 passing from outside of the endoscope 12 (i.e., from inside the body cavity), through the window 34, to the second reflector 32, to the first reflector 30, and then to a CCD camera 38 positioned in the proximal end portion 24 of the endoscope 12. In the embodiment depicted in FIG. 3, a rod lens 40 transmits light between the first reflector 30 and the camera 38, so that the optical path 36 passes along the rod lens 40. The optical path 36 is thus broken into three portions. The first optical path portion 42 passes from the camera 38 to the first reflector 30; the second optical path portion 44 passes from the first reflector 30 to the second reflector 32; and the third optical path portion 46 passes from the second reflector 32 out through the window 34. Various lenses 47 are positioned along the optical path 36 to help concentrate and focus images.

In the embodiment of FIG. 3, the first reflector 30 is rigidly secured to the interior of the endoscope 12, while the second reflector 32 is rotatably mounted in the endoscope 12 to permit the second reflector 32 to be rotated about an axis 48 generally aligned with the second optical path portion 44 adjacent to the second reflector 32. Rotation of the second reflector 32 about its axis 48 does not move or otherwise disrupt the second optical path portion 44, but that rotation does cause the third optical path portion 46 to "sweep" through viewing angles equivalent to the angular rotation of the second reflector 32. Thus, the camera 38 is provided with images from the viewing angles swept through by the third optical path portion. For example, a 30 degree rotation of the second reflector 32 will cause the camera to receive images corresponding to a 30 degree sweep of the third optical path.

Various techniques may be employed to control rotation of the second reflector. A small actuator motor may be used, such as one positioned at the distal end portion of the endoscope to rotate the second reflector in response to signals received from a user. The second reflector may be rotated by mechanical means, such as a system of actuator motors, pull lines or wires, and/or a gearing system such as that depicted in FIG. 3. Other control techniques could also be used without departing from the scope of the invention.

In order to control the rotation of the second reflector 32, the embodiment of FIG. 3 includes a gearing system that includes a second reflector gear 50 to which the second reflector 32 is secured. The second reflector gear 50, which rotates about the second reflector axis 48, is meshed to a distal gear 52 secured to a gear shaft 54 that passes generally along the length of the endoscope shaft 23. Secured to the proximal end of the gear shaft 54 is a proximal gear 56, which in the embodiment depicted is a spur wheel gear. The proximal gear 56 is meshed to a rotator control gear 58, which in the embodiment shown is a crown gear. The rotator control gear is secured to a rotator control knob 60.

A person skilled in the optical arts will note that rotation of the second reflector 32 about its rotational axis 48 will cause the image received by the camera 38 to rotate in a manner that can be awkward for a user to view and comprehend. To compensate for this effect, the invention in the embodiment of FIG. 3 has the camera 38 rotatably secured to the endoscope shaft 23 to permit its rotation about an axis 62 generally aligned with the first optical path portion 42 adjacent to the camera 38. Rotation of the camera 38 is controlled to correspond to rotation of the second reflector 32. In the embodiment depicted in FIG. 3, the camera is secured to a camera gear 64, which is depicted as a spur wheel gear, having an axis 62 aligned with the first optical path portion 42 adjacent to the camera 38. The camera gear 64 is meshed to the proximal gear 56 of the gear shaft 54. In the embodiment shown, the gearing assembly is engineered such that inducing rotation of the second reflector 32 causes an equivalent amount of rotation of the camera 38. For example, rotating the second reflector 32 by 90 degrees will cause the camera 38 to rotate by 90 degrees, i.e., a one-to-one ratio between the corresponding rotations of the camera 38 and second reflector 32. Other corresponding rotation ratios between the camera and second reflector may also be used, depending on a particular apparatus.

An important issue for endoscopes is the ability of the user to determine in which direction the endoscope is "looking." Failure to know precisely the direction in which the endoscope is looking can complicate a procedure. Accordingly, it is preferred that the user have a reference indicating the viewing position of the endoscope.

The rotator controller of the current invention can serve the function of indicating the viewing angle of the endoscope. In the embodiment depicted in FIGS. 2 and 3, the rotator controller knob 60 is configured to indicate the viewing angle of the endoscope 12. The rotator knob 60 is rotatably secured to the proximal end portion 24 of the endoscope 12, with the rotator knob rotational axis 66 parallel to the second reflector rotational axis 48. Moreover, the gearing assembly between the rotator knob 60 and second reflector 32 is configured such that rotation of the rotator knob 60 causes an equivalent rotation (i.e., a one-to-one corresponding rotation) of the second reflector. For example, a ninety-degree rotation of the rotator knob 60 will cause a ninety-degree rotation of the second reflector 32.

To further assist the user in determining the viewing angle, the rotator knob 60 may include markings or other indicia that show the viewing angle of the endoscope 12. For example, in the embodiment depicted in FIG. 2, the rotator knob 60 includes a marking 68 indicating the rotational position of the knob 60, which, in the case where the rotator knob 60 and second reflector 32 have corresponding rotations, also serves to indicate the rotational position of the second reflector 32, thus depicting the viewing angle of the endoscope 12.

During a surgical procedure, a user may be keeping his or her eyes on the video monitor receiving images from the camera. Thus, the user may not have much opportunity to actually look at the position of the rotator knob. Accordingly, the positional markings on the rotator knob may include surface indicators that can be easily detected by touch, such as variances in surface texture or form. These may include raised, lowered, or roughened surfaces. Thus, the user can know the position of the knob, and hence the viewing angle, by merely touching the knob, without necessarily having to take his or her eyes off of the monitor to actually see the knob.

In the embodiment of FIG. 2, the marking 68 is a raised arrow, with the arrow aligned to be parallel with the third optical path portion 46 passing from the second reflector 32 out of the viewing window 34. Thus, the arrow's rotational position indicates the actual viewing angle of the endoscope 12.

Figure 4B:
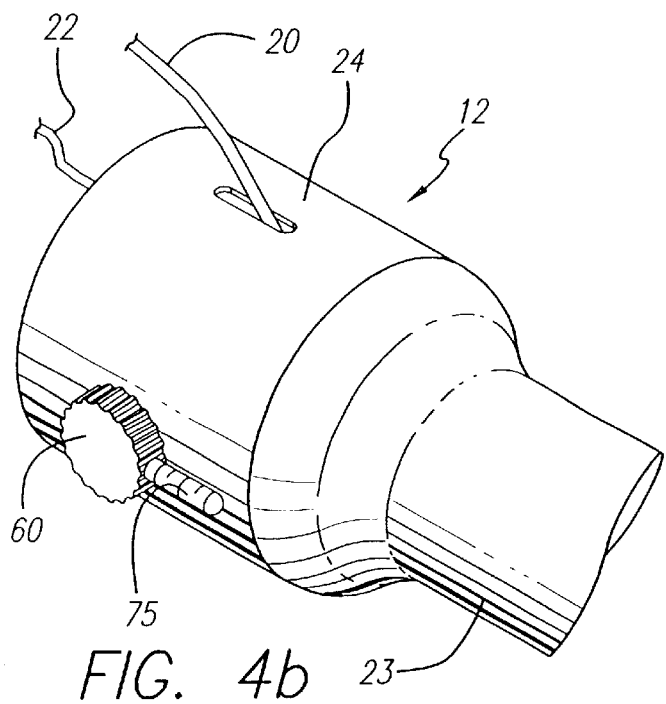
FIG. 4b is a perspective view of a proximal portion of an endoscope in accordance with an embodiment of the invention.

The indicia may comprise a series of one or more raised portions on the rotator knob 60, such as one or more raised dots. For example, in the embodiment of FIG. 4a, the indicia is a combination of a central raised dot 70 with a series of outer raised dots 72, 74. In the embodiment of FIG. 4b, the indicia is a pointer 75 extending from the rotator knob 60. Like the raised arrow of FIG. 3, the central raised dot 70 and outer raised dots 72, 74 of the embodiment in FIG. 4a and the pointer 75 of FIG. 4b are aligned so as to be parallel to the third optical path portion 46 passing from the second reflector 32 out of the viewing window 34. Thus, the raised dots 70, 72, 74 or pointer 75 indicate the line of sight of the endoscope 12.

Figure 4C:
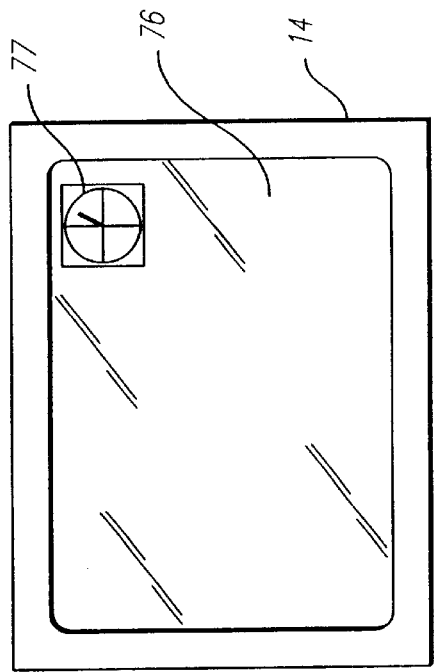
FIG. 4c is a front view of a video monitor in accordance with an embodiment of the invention.

In a further embodiment, an outside display may indicate the viewing angle of the endoscope, such as where the endoscope provides a signal to a monitor to represent the viewing angle. For example, the rotator knob may include sensors or other devices that provide rotational position signals to a video monitor, with the video monitor providing a numerical, graphical, or other representation of the viewing angle. In the embodiment depicted in FIG. 4c, the monitor 14 that provides images of the interior of the cavity on its main screen 76 also depicts a graphical representation 77 of the viewing angle.

In the embodiment of FIGS. 1–3, illumination is provided by an external illumination source 16 that provides light through a light-transmitting cable 20. The light transmitting cable 20 connects to one or more illumination fibers 78 that pass alongside the rod lens 40 and transmit the light to the first reflector 30, where the light is reflected off of the first reflector 30, to the second reflector 32, and then out of the window 34 to the cavity 18.

In the embodiment depicted in FIG. 3, the optical path portions 42, 44, 46 are generally straight and unobstructed. However, the optical path 36 and its portions 42, 44, 46 may include additional optical assemblies, such as rod lenses or mirrors, that may bend or otherwise divert the optical path portions 42, 44, 46 out of the straight paths depicted. For example, in the embodiment depicted in FIG. 5, the first optical path portion 42, i.e., the portion between the camera 38 and the first reflector 30, includes a flexible fiber-optic bundle 80 with an objective lens 81 at either end. The flexible fiber-optic bundle 80 permits the shaft 23 of the endoscope 12 to be curved or bent without causing a break in the optical path 36, as may be necessary for the shaft 23 to pass through tortuous curves in a body passage. Such a feature could permit construction of a rigid but non-straight (e.g., curved) endoscope shaft, or even of a flexible endoscope shaft.

Figure 7:
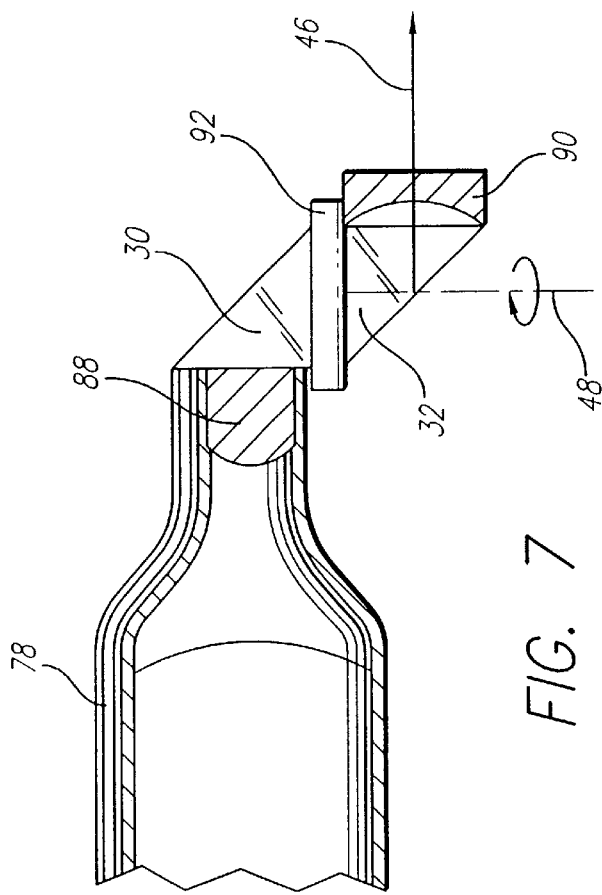
FIG. 7 is a cross-sectional side view of a distal portion of an endoscope, according to an embodiment of the invention.

FIGS. 6 through 8 depict additional embodiments of the invention, with variations to the optical assemblies. In FIG. 6, a rod lens relay system 82 is positioned along the first optical path portion 42, with the rod lens system 82 including a series of small rod lenses 84 aligned along the first optical path portion 42. Various objective lenses 86 are used to concentrate and focus the images along the optical path.

The first and second reflectors themselves may be varied within the scope of the invention. For example, the prisms depicted in the various embodiments may be replaced with mirrors or other reflective and/or refractive devices without departing from the scope of the invention. Note that the term "reflector" is, in the terms of this application, considered to encompass any device that diverts the passage of light. Additionally, various optical assemblies, such as filters and/or objective lenses, may be positioned in the optical path to enhance the images received by the camera. For example, FIG. 7 depicts two objective lenses, with a positive objective lens 88 positioned against the first reflector 30 along the first optical path portion 42, and a negative objective lens 90 positioned against the second reflector 32 along the third optical path portion 46. FIG. 7 further includes a spacer 92 that may be employed to maintain the spacing between the first reflector 30 and second reflector 32. The spacer 92 thus serves to assist in securing the reflectors in their desired positions, which can prevent damage to the reflectors if the endoscope is dropped or otherwise roughly handled. The spacer 92 may be formed from a lubricious material that seals the adjacent reflector surfaces from contamination while permitting the second reflector 32 to freely rotate.

Returning to FIG. 3, the gear shaft 54 is hollow, defining a channel 94 therein. The channel 94 passes from the outside of the proximal end portion 24 and terminates at an opening 96 in the distal end portion 26 of the endoscope 12. In the embodiment of FIG. 3, an O-ring 98 is positioned at the distal end of the gear shaft 54 so as to have the channel 94 open to the body cavity while maintaining a seal of other portions of the endoscope 12. Accordingly, the channel 94 may, depending on its size, be used as an irrigation channel for the introduction and/or removal of irrigating fluids to the cavity. The channel 94 may also serve as an access channel for the introduction of tools, such as surgical tools, to the cavity.

In other embodiments of the invention, several channels may be provided in the endoscope, including separate channels for fluid introduction, fluid removal, and instrument introduction. For example, in the embodiment of FIG. 8, three separate channels are provided in the distal end portion 26 of an endoscope 12. An irrigation channel 100 serves to introduce fluids into the cavity, while a separate fluid removal channel 102 can simultaneously remove fluids. A larger instrument introduction channel 104 permits surgical tools to be introduced into the cavity.

Figure 9A:
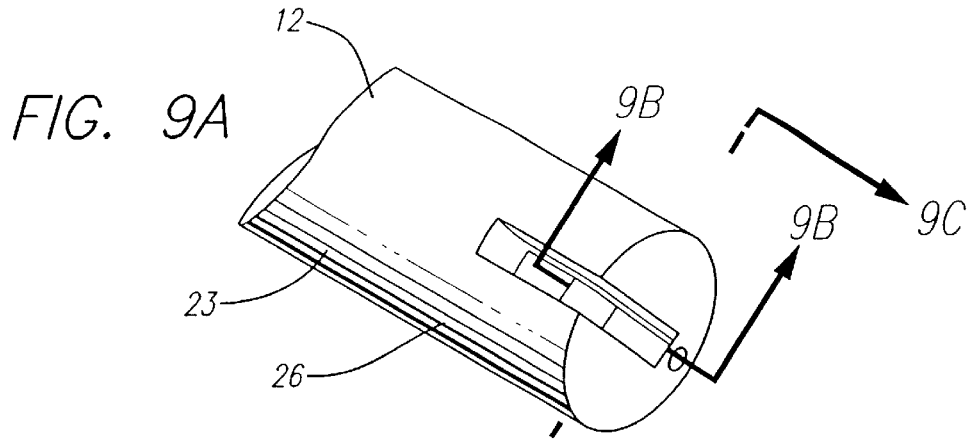
FIG. 9a is a perspective view of a distal portion of an endoscope, according to an embodiment of the invention.
Figure 9B:
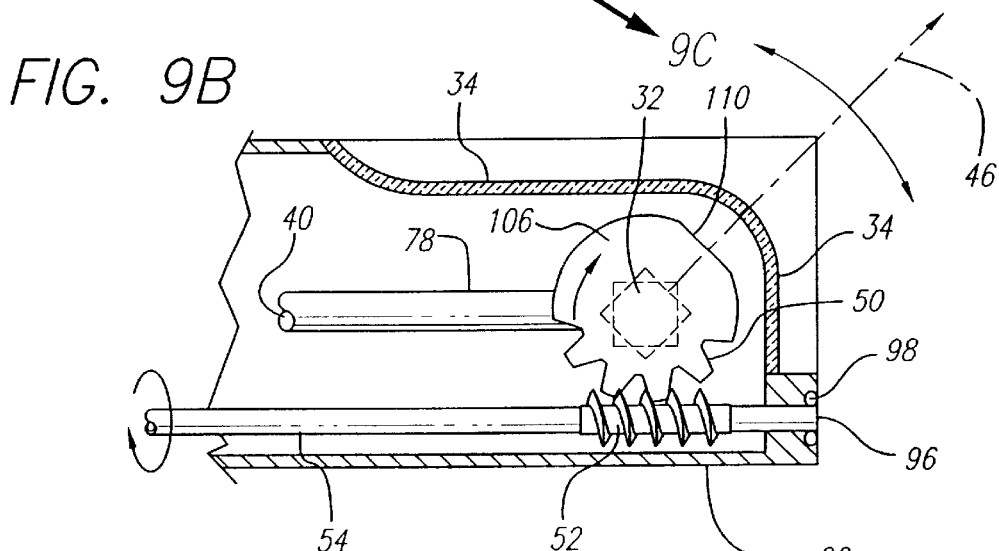
Figure 9C:
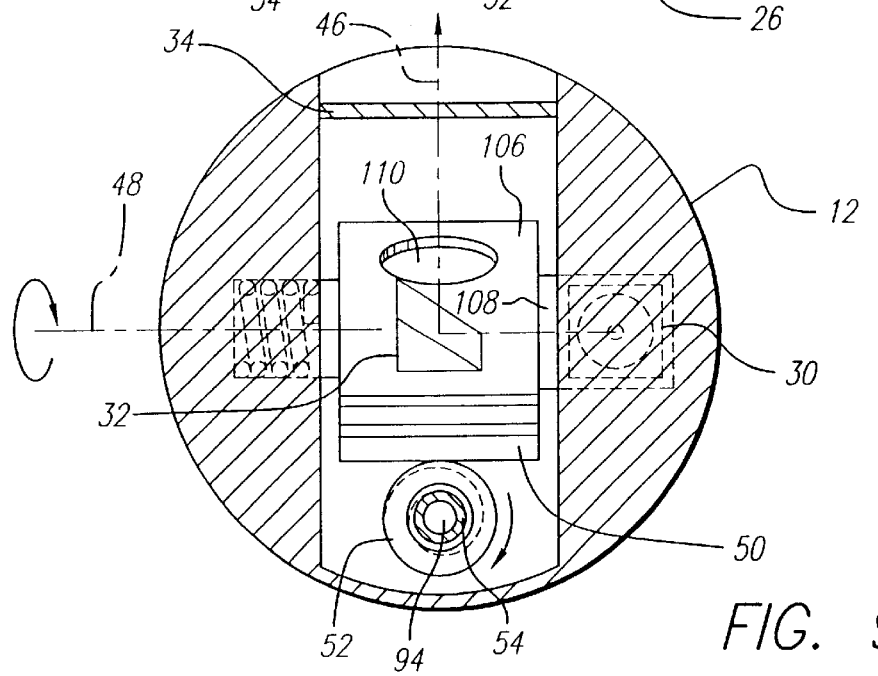

Various embodiments of the endoscope distal end portion 26 are within the scope of the invention. In the embodiment depicted in FIG. 3, the window 34 comprises a fixed transparent cover that seals the endoscope, thereby protecting the optical assembly within, including the first reflector 30 and second reflector 32. FIGS. 9a, 9b, and 9c depict the distal end portion 26 of an endoscope similar to that in FIG. 3. FIG. 9b depicts the distal end portion 26 in partial crosssection along the line 9B—9B depicted in FIG. 9a, while FIG. 9c depicts a partial cross-section along the line 9C—9C. In the embodiment depicted, the second reflector 32 is secured within a rotatable housing 106 that includes a small side opening 108 that allows light to pass between the second reflector 32 and the first reflector 30. A viewing opening 110 allows light to pass between the second reflector and the window 34. The window 34 is large enough to cover the entire "sweep" angle through which the second reflector 32 can view, with the window 34 serving to allow light to pass while sealing the entire assembly against outside contamination. Such sealing can make the device easier to sterilize. The housing 106 is rotatably mounted to permit rotation with the second reflector 32 about the second reflector's rotational axis 48.

In another embodiment, the second reflector is mounted in a rotatable housing that is configured so that it can be positioned on the outside of the endoscope shaft. For example, in the embodiment shown in FIGS. 10a and 10b, a rotatable housing 112 containing the second reflector 32 can be moved from inside the endoscope shaft 23 to the outside of the endoscope shaft 23. In the extended position depicted in FIG. 10a, the housing 112 is positioned on the outside of the endoscope main shaft 23. The window 34 is located directly on the rotatable housing 112, so that the window 34 rotates with the second reflector 32. By positioning the rotational housing 112 of FIG. 10a on an external portion of the endoscope shaft 23, the rotational housing 112, and therefore the second reflector 32, can be rotated 360 degrees about an axis 48 perpendicular to the longitudinal axis 27 of the endoscope 12. When such a 360 degree rotation of the second reflector 32 is combined with a 360 degree rotation of the endoscope main shaft 23 about its longitudinal axis 27, complete spherical viewing of the body cavity can be achieved.

Figure 10A:
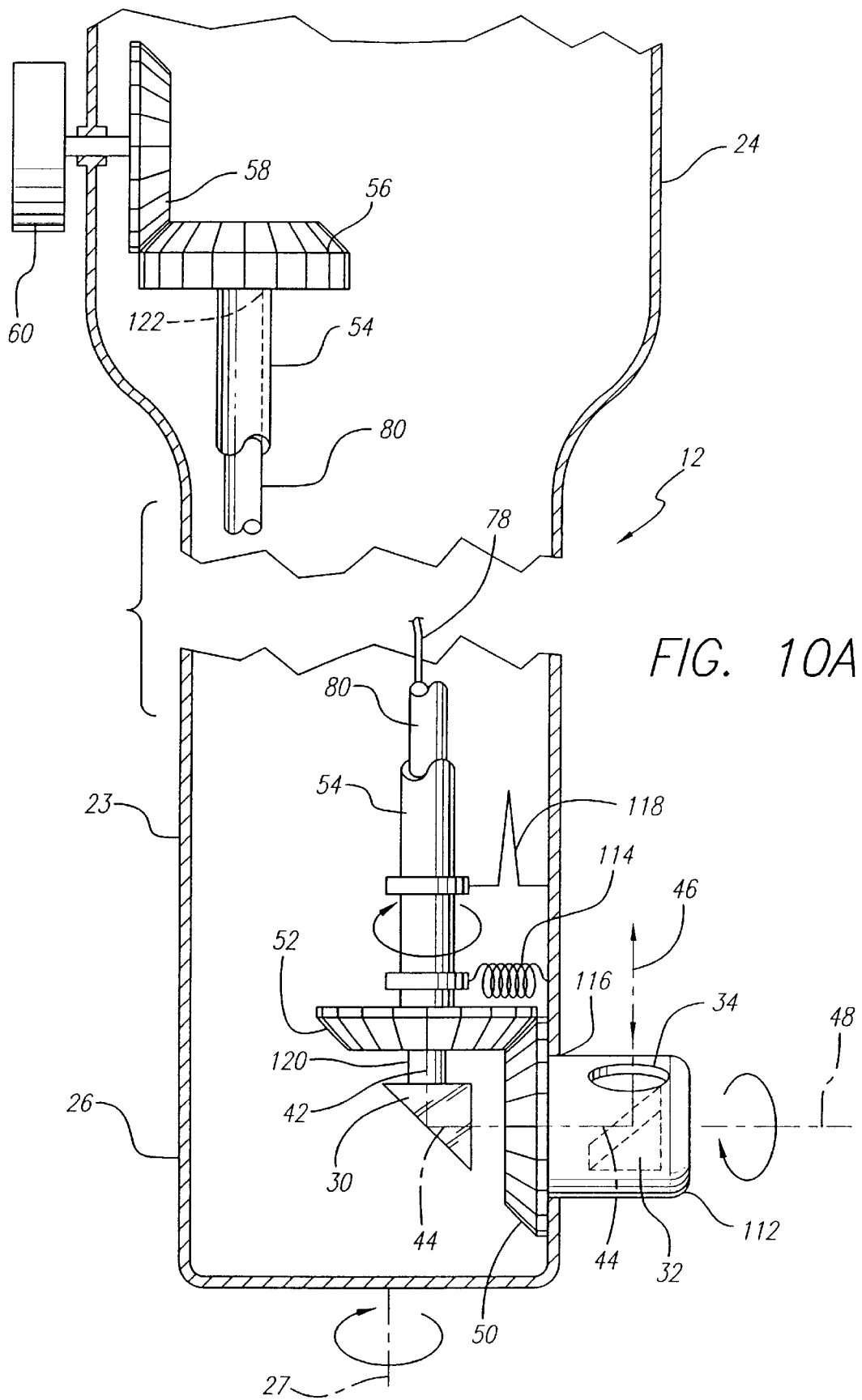
FIGS. 10a and 10b are cross-sectional side views of an endoscope, according to an embodiment of the invention.
Figure 10B:
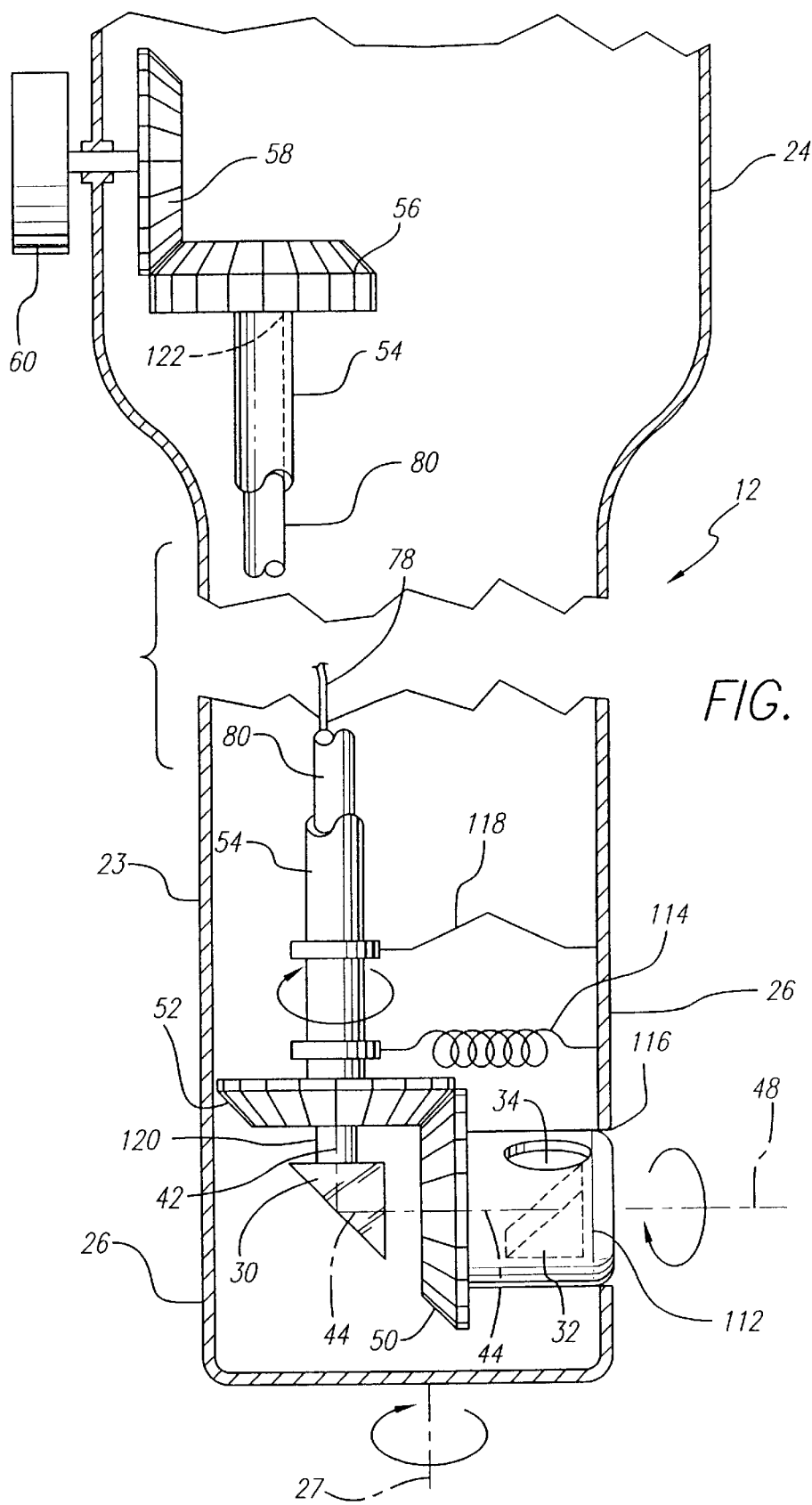

As depicted in FIG. 10b, the housing 112 can be retracted into the endoscope shaft 23, which may facilitate the endoscope's insertion into and removal from the cavity being viewed. Various devices can be used to retract and deploy the housing 112. In the embodiment depicted in FIG. 10b, the housing 112 is biased toward the retracted position by a spring 114 that urges the gear shaft 54, and hence the housing 112, away from an opening 116 in the endoscope shaft 23. Extending the housing 112 out of the shaft 23 is achieved by an electromagnet 118 that, when activated by sufficient voltage to overcome the resistance of the spring 114, urges an opposite movement of the gear shaft 54 so as to cause the housing 112 to assume the extended position depicted in FIG. 10a. Because the spring 114 is constantly urging the housing 112 to the retracted position of FIG. 10b, an accidental or intentional interruption of power to the electromagnet 118 will cause the housing 112 to retract. Note that, in the embodiment of FIGS. 10a and 10b, the spring 114 and electromagnet 118 are secured to the shaft so as to permit the gear shaft 54 to freely rotate about its axis. In the embodiment depicted, the retracted housing 112 is sized to assist, in both the retracted and expanded positions, in maintaining a seal about the opening 116 in the endoscope shaft 23, thereby preventing the admission of contaminants into the endoscope shaft 23.

Also in FIGS. 10a and 10b, the fiber-optic bundle 80 of the first optical path portion 42, and the illumination line 78, are positioned within the hollow gear shaft 54. Although the alignment of the gear shaft 54 and fiber-optic bundle 80 appears to be offset in FIGS 10a and 10b between the endoscope distal portion 26 and the endoscope proximal portion 24, they are in fact aligned. The apparent misalignment is caused by the "break" in the each figure between the ends of the endoscope, and is further exaggerated by the endoscope length being much larger as compared to the endoscope width.

The fiber-optic bundle 80 and illumination line 78 may be configured to remain stationary when the hollow gear shaft 54 rotates around them. As an alternative approach, a fiber-optic bundle such as that depicted in FIGS. 10a and 10b can be secured at its distal end 120 so that the distal end 120 remains stationary when the control knob 60 and gear shaft 54 are rotated, but the fiber-optic bundle proximal end 122 is secured or geared such that it rotates with the gear shaft 54 and/or control knob 60 so that the proximal end 122 of the fiber-optic bundle 80 will rotate by an amount corresponding to the rotation of the second reflector 32. This "twisting" of the fiber-optic bundle will result in the image at the proximal end 122 of the bundle 80 being rotated. Thus, there is no need to rotate a camera to compensate for rotation of the second reflector. Such an assembly can be used with a remote camera that may receive optical signals from the endoscope via a fiber-optic line. Such an assembly could also be used without any camera, with a user using an eyepiece to "directly" view the image supplied by the fiber-optic bundle 80 and other optics present.

Figure 11:
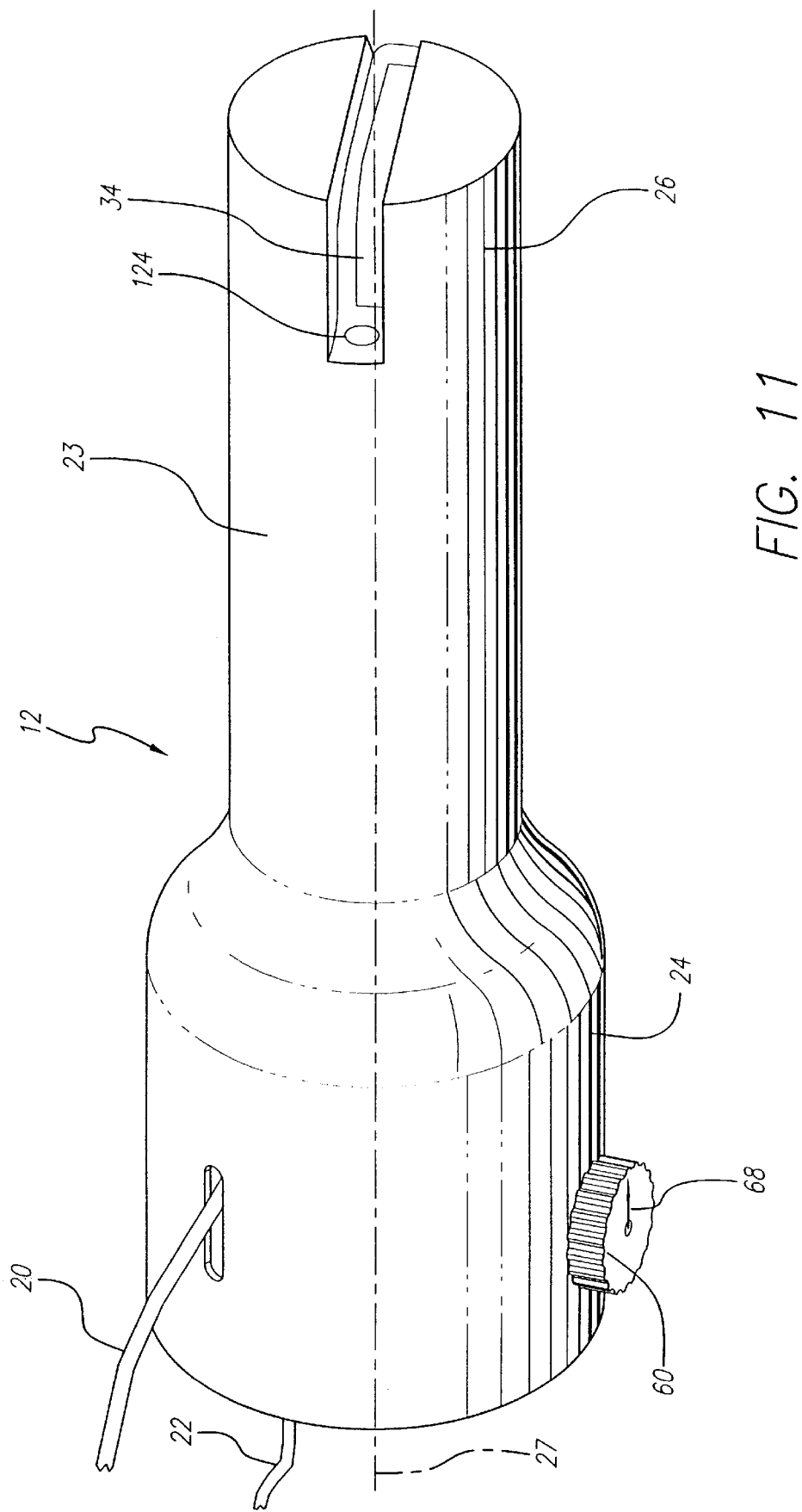
FIG. 11 is a perspective view of an endoscope, according to an embodiment of the invention.
Figure 12:
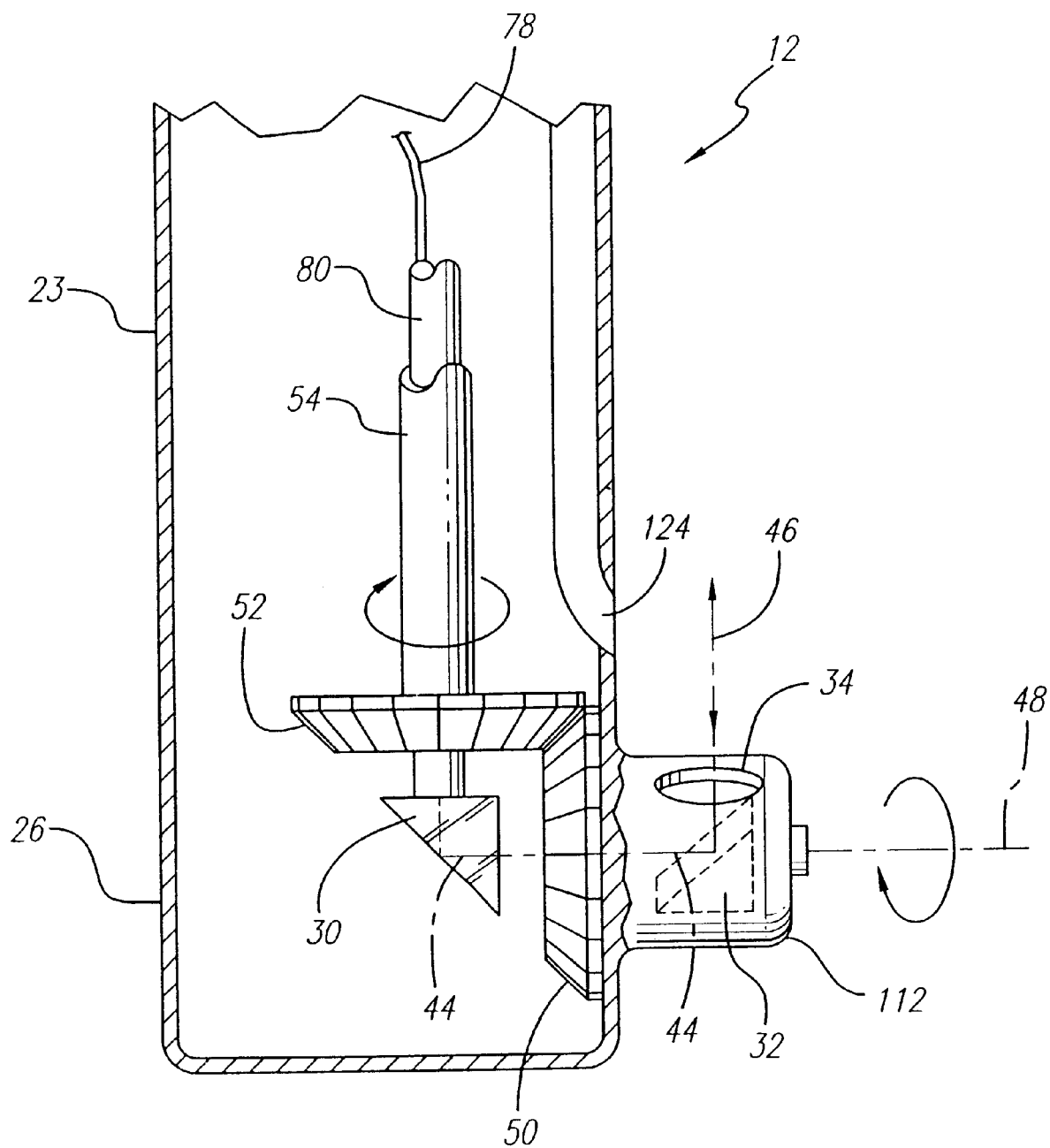
FIG. 12 is a cross-sectional side view of a distal end portion of an endoscope, according to an embodiment of the invention.

In order to keep a viewing window formed of solid material (as opposed to an open window) clean of debris, an irrigation channel can be positioned so as to provide a fluid flow that passes over the window. For example, in FIG. 11, which is similar to the embodiment of FIG. 3, an irrigation channel opening 124 is positioned so that the fluid flow passes along the surface of the window 34, thereby washing debris off of the window 34. In FIG. 12, which is similar to the embodiment of FIG. 10, the irrigation channel opening 124 is positioned so that, when the housing 112 is rotated to a certain position, an irrigation flow passes over the window 34. Thus, a user can clean the window 34 by rotating the housing 112 into a position adjacent the irrigation channel 124.

Figure 13:
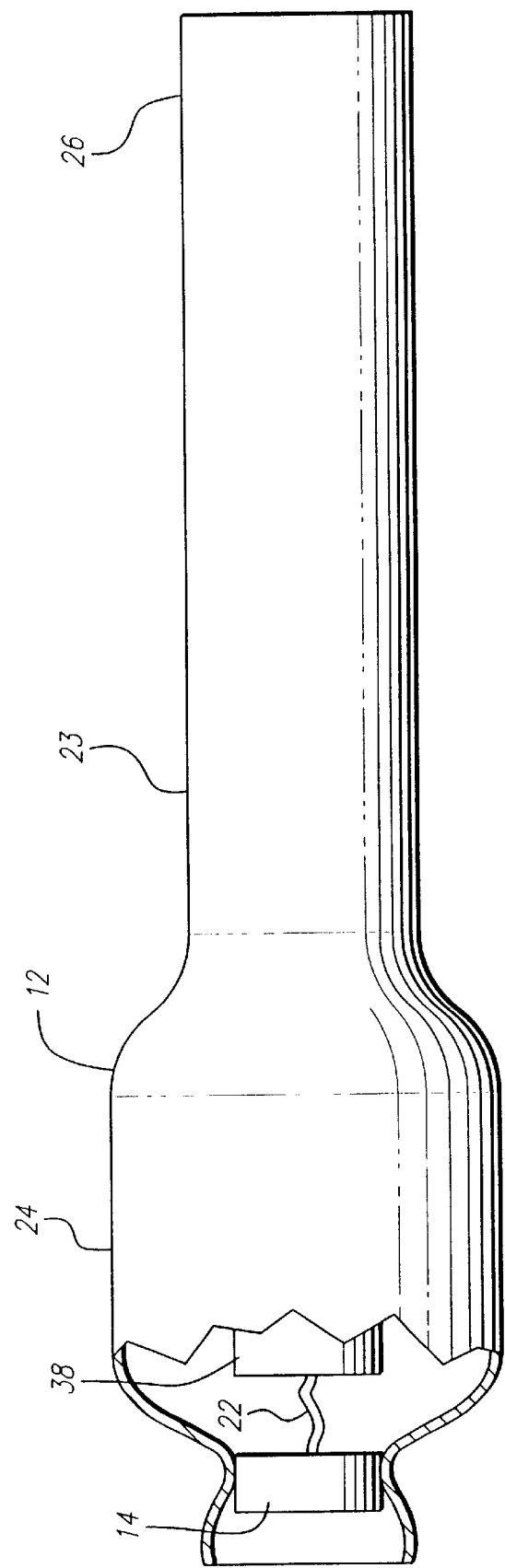
FIG. 13 is a side view, in partial cross-section, of an endoscope, according to an embodiment of the invention.

Other embodiments (such as FIG. 1) of the invention have a monitor positioned apart from the endoscope, but a monitor may be positioned on the endoscope itself. For example, in the embodiment depicted in FIG. 13, the endoscope 12 includes a monitor 14 secured to the proximal portion of the endoscope 12. The monitor 14 is relatively small, and is positioned to generally mimic the position of an eyepiece on a conventional endoscope. Thus, a user who is accustomed to conventional endoscopes equipped with eyepieces may be more comfortable using the endoscope-mounted monitor 14 than he or she would be viewing a surgical procedure on a large monitor separate from the endoscope. The endoscope-mounted monitor 14 may thus be used in lieu of, or in addition to, an external monitor such as the one depicted in FIG. 1.

Figure 14:
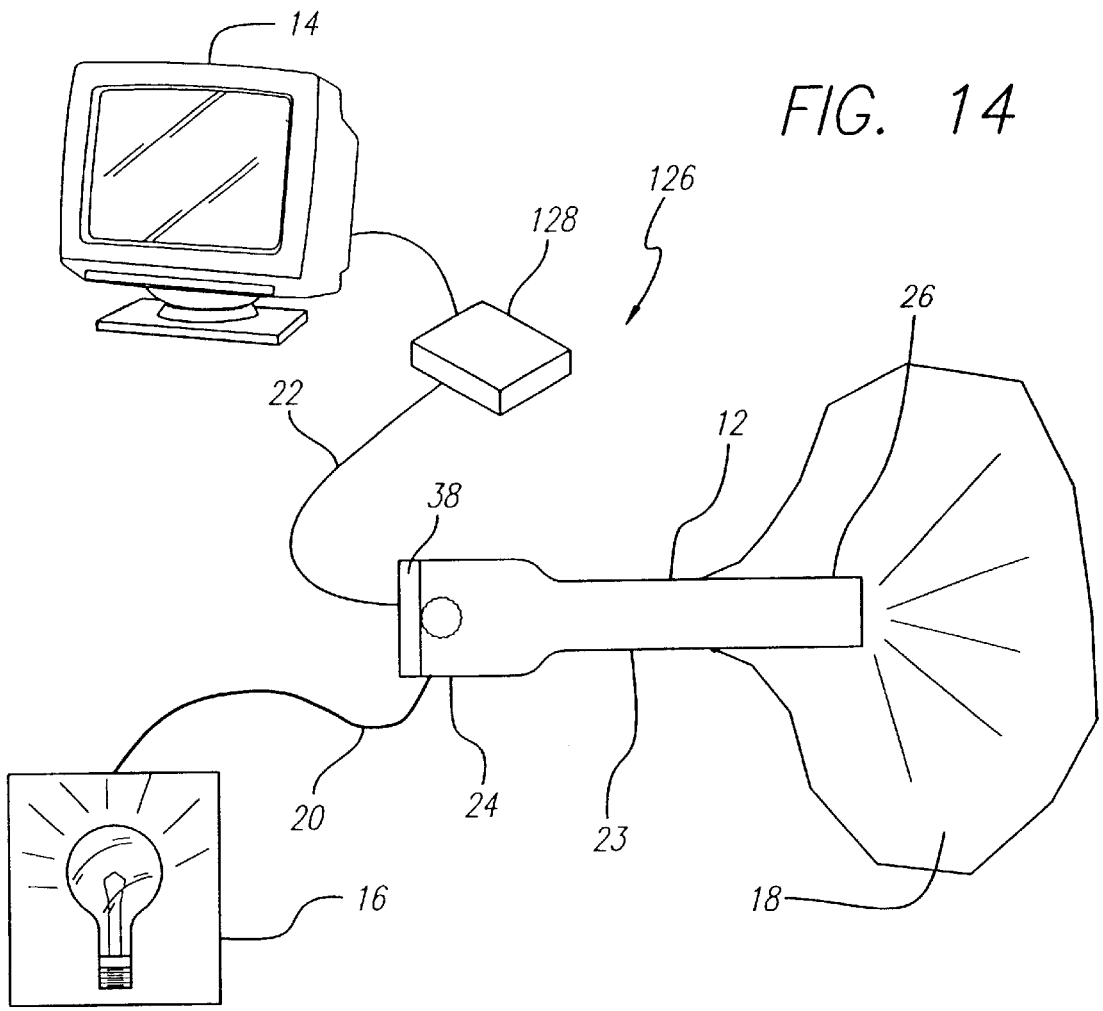
FIG. 14 is a view of an endoscopic viewing system according to an embodiment of the invention.

FIG. 14 depicts another embodiment of the invention, wherein an endoscopic system 126 includes an endoscope 12 with a camera 38 rigidly mounted to the endoscope 12, as opposed to the rotational mounting depicted in other embodiments. To correct for undesirable viewing problems caused by rotation of the second reflector, the system 126 of FIG. 14 includes a processor 128 that receives the image signals from the camera 38, and then processes the signals to compensate for the rotation of the second reflector. The processing of the signals includes: (1) receiving a position signal from the endoscope 12 indicating the rotational position of the second reflector; (2) "rotating" the image from the camera 38 by an angle corresponding to the angle of rotation of the second reflector; and (3) providing a rotated image to the monitor 14, with the rotation of the image corresponding to the rotation of the second reflector. Such a rotation of the image can be achieved through relatively simple processing.

Figure 15:
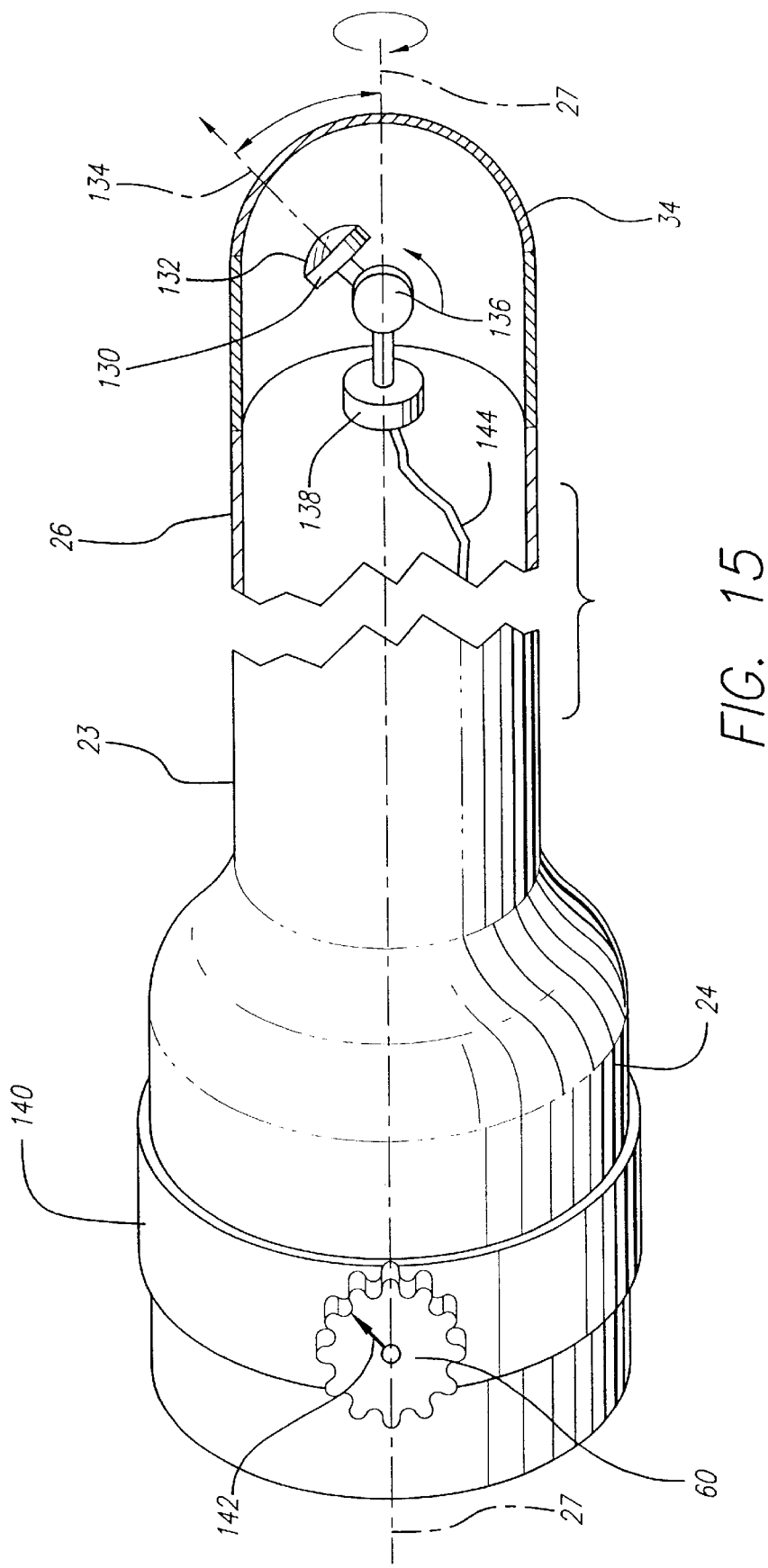
FIG. 15 is a perspective view, in partial cross-section, of an endoscope in accordance with an embodiment of the invention.

FIG. 15 depicts a further embodiment, wherein the optical lens assembly is replaced with a small camera 130, such as a CCD camera, which is itself positioned at the distal end portion 26 of the endoscope 12. The camera 130, which in the embodiment depicted has an objective lens 132 positioned at its face, provides a view about a line of sight 134. The camera 130 is mounted in the endoscope 12 so as to permit the camera 130 to be rotated to move its line of sight 134 to almost any desired viewing angle. In the embodiment depicted, the camera 130 is secured to a first actuator device 136, which may include an actuator motor, configured to rotate the camera 130 about an axis perpendicular to the longitudinal axis 27 of the endoscope 12. The first actuator device 136 is itself mounted on a second actuator device 138 configured to rotate about an axis generally aligned with the longitudinal axis 27 of the endoscope 12. The first actuator device 136 and second actuator device 138 are controlled by a control device, depicted as a control knob 60 secured to a rotating band 140, positioned at the proximal end portion 24 of the endoscope 12, which provides control signals through control lines 144 passing through the endoscope 12.

In the embodiment of FIG. 15, the control knob 60 is secured to the rotatable band 140 passing around the distal end portion 26 of the endoscope 12. The control knob 60 includes indicia, in this case a raised arrow 142, that indicates the line of sight 134 of the camera 130. The control knob 60 provides signals to the first actuator device 136, so that rotation of the control knob 60 causes a corresponding rotation of the first actuator device 136 (and hence a rotation of the camera 130) about an axis perpendicular to the longitudinal axis 27 of the endoscope. For example, for a one-to-one (i.e., equivalent) correspondence, a 90 degree rotation of the control knob 60 will cause a 90 degree rotation of the first actuator device 136 and camera 130. Similarly, the rotatable band 140 provides signals to the second actuator device 138, so rotation of the rotatable band 140 about the longitudinal axis 27 of the endoscope 12 causes a corresponding rotation of the second actuator device 138, thereby causing rotation of the camera 130 about the longitudinal axis 27 of the endoscope 12. By having the physical position of the knob 60 and its marking 142 aligned with the line of sight 134 of the camera 130, a user can easily determine and understand the angle of the camera line of sight 134.

Other assemblies may also be used to control the position of the camera line of sight 134 in embodiments having the camera positioned in the distal end portion 26. For example, a system of gears, such as that depicted in the embodiment of FIG. 3 of this application, could be used to control the camera line of sight. A system of wires and pulleys might also be used.

Although preferred and alternative embodiments of the invention have been described and illustrated, the invention is susceptible to modifications and adaptations within the ability of those skilled in the art and without the exercise of inventive faculty. Thus, it should be understood that various changes in form, detail, and usage of the present invention may be made without departing from the spirit and scope of the invention. For example, while the specific embodiments set forth herein are directed toward endoscopes for use in surgical procedures, it is apparent that the apparatus would have use in various other applications where viewing of remote areas is desired. Accordingly, it is not intended that the invention be limited, except as by the appended claims.

What is claimed is:

1. An apparatus for examining the interior of a cavity, comprising:

a generally tubular member having a distal end portion and a proximal end portion;

a camera rotatably secured to the tubular member;

a first reflector positioned in the distal end portion of the tubular member;

a second reflector rotatably positioned in the distal end portion of the tubular member, said second reflector positioned so as to be optically aligned with the camera through the first reflector, whereby an optical path is defined between the camera, the first reflector, and the second reflector, and whereby the optical path comprises a first optical path portion passing between the camera and the first reflector, and a second optical path portion passing between the first reflector and the second reflector;

a viewing window positioned at the distal end portion of the tubular member, said viewing window positioned so as to be optically aligned with the camera and the first reflector through the second reflector, whereby the optical path further comprises a third optical path portion passing between the second reflector and the viewing window;

a rotator for selectively rotating the second reflector about an axis generally aligned with the second optical path portion, and for selectively rotating the camera about an axis generally aligned with the first optical path portion.

2. The apparatus of claim 1, wherein the rotator controls rotation of the camera and the second reflector to cause corresponding rotations of the camera and of the second reflector.

3. The apparatus of claim 2, wherein the rotator controls rotation of the camera and the second reflector to cause equivalent rotations of the camera and of the second reflector.

4. The apparatus of claim 3, further comprising:
   a television monitor for receiving image signals from the camera and for providing a display based on the received image signals.

5. The apparatus of claim 1, wherein the apparatus further comprises:
   an opening in the distal end portion of the tubular member; and
   a channel passing from the tubular member proximal end portion to the tubular member distal end opening.

6. The apparatus of claim 5, wherein the channel comprises an irrigation channel for providing an irrigating fluid.

7. The apparatus of claim 6 for providing an irrigation fluid, wherein the distal end opening provides a stream of irrigating fluid, and the distal end opening is positioned so as to cause the irrigating fluid stream to pass over the viewing window, whereby the irrigating fluid stream removes debris from the viewing window.

8. The apparatus of claim 1, wherein the rotator comprises:
   a gear shaft passing generally parallel a central axis of the tubular member, said gear shaft having a proximal end portion and a distal end portion;
   a distal gear secured to the distal end portion of the gear shaft, said distal gear having an axis of rotation in general alignment with the gear shaft;
   a reflector gear mechanically meshed with the distal gear, said reflector gear being rigidly secured to the second reflector, said reflector gear having an axis of rotation in axial alignment with the axis of rotation of the second reflector, said reflector gear mechanically linked with the distal gear, whereby rotation of the gear shaft and distal gear causes a corresponding rotation of the reflector gear and second reflector.

9. The apparatus of claim 8, further comprising:
   a distal opening in the distal end portion of the tubular member; and
   a channel passing through the gear shaft from the gear shaft proximal end portion to the gear shaft distal end portion; and
   wherein the gear shaft channel is aligned with the distal opening of the tubular member, thereby defining an open channel passing from the distal opening to the gear shaft proximal end portion.

10. The apparatus of claim 9, wherein the open channel comprises an irrigation channel for providing an irrigating fluid.

11. An apparatus for examining the interior of a cavity, comprising:
   a generally tubular member having a distal end portion and a proximal end portion;
   a viewer positioned at the proximal end portion of the tubular member;
   a first reflector positioned in the distal end portion of the tubular member;
   a second reflector rotatably positioned in the distal end portion of the tubular member, said second reflector positioned so as to be optically aligned with the viewer through the first reflector, whereby an optical path is defined between the viewer, the first reflector, and the second reflector, and whereby the optical path comprises a first optical path portion passing between the viewer and the first reflector, and a second optical path portion passing between the first reflector and the second reflector;
   a viewing window positioned at the distal end portion of the tubular member, said viewing window positioned so as to be optically aligned with the viewer and the first reflector through the second reflector, whereby the optical path further comprises a third optical path portion passing between the second reflector and the viewing window;
   a rotator for selectively rotating the second reflector about an axis generally aligned with the second optical path portion, said rotator comprising a rotating knob secured to the proximal end portion of the tubular member, wherein rotation of the rotating knob causes a corresponding rotation of the second reflector,
   a rotation indicator for indicating to a user the rotational position of the second reflector, wherein the rotation indicator comprises a marking on the rotating knob,
   wherein the rotator knob rotates about a knob axis generally parallel to the axis of rotation of the second reflector, and wherein rotation of the rotator knob causes an equivalent rotation of the second reflector, and wherein the rotating knob marker is positioned on the rotator knob so that a line passing from the rotating knob marker to the rotating knob axis defines a line parallel to the third optical path portion passing between the second reflector and the viewing window.

12. The apparatus of claim 11, wherein the marking is a raised portion on the knob surface.

13. An apparatus for examining the interior of a cavity, comprising:
   a generally tubular member having a distal end portion and a proximal end portion;
   a camera secured to the tubular member, said camera for providing an image;
   a first reflector positioned in the distal end portion of the tubular member;
   a second reflector rotatably positioned in the distal end portion of the tubular member, said second reflector positioned so as to be optically aligned with the camera through the first reflector, whereby an optical path is defined between the camera, the first reflector, and the second reflector, and whereby the optical path comprises a first optical path portion passing between the camera and the first reflector, and a second optical path portion passing between the first reflector and the second reflector;
   a viewing window positioned at the distal end portion of the tubular member, said viewing window positioned so as to be optically aligned with the camera and the first reflector through the second reflector, whereby the optical path further comprises a third optical path portion passing between the second reflector and the viewing window, with said third optical path portion generally aligned with a viewing angle of the apparatus;

a rotator for selectively rotating the second reflector about an axis generally aligned with the second optical path portion;

a processor configured to (a) receive the image from the camera, (b) receive a rotational signal, (c) rotate the received image as a function of the rotational signal, and (d) provide a rotated image; and a monitor to display the rotated image.

14. The apparatus of claim 13, wherein the monitor is further configured to display a representation of the viewing angle.

\* \* \* \* \*

UNITED STATES PATENT AND TRADEMARK OFFICE
CERTIFICATE OF CORRECTION

PATENT NO. : 6,371,909 B1  Page 1 of 1
DATED : April 16, 2002
INVENTOR(S) : Hans D. Hoeg et al.

It is certified that error appears in the above-identified patent and that said Letters Patent is hereby corrected as shown below:

Title page,
Item [56], U.S. PATENT DOCUMENTS, add the following patents:
-- 4,890,159    12/1989    Ogiu
   5,895,350    4/1999     Hori
   5,994,655    8/1999     Becker --.
FOREIGN PATENT DOCUMENTS, add the following patent
-- GB    1,477,070    6/1977 --.

Signed and Sealed this

Seventeenth Day of September, 2002

Attest:

Attesting Officer

JAMES E. ROGAN
*Director of the United States Patent and Trademark Office*